(12) United States Patent
Bevinakatti et al.

(10) Patent No.: US 8,673,987 B2
(45) Date of Patent: Mar. 18, 2014

(54) SURFACTANT COMPOSITION

(75) Inventors: Hanamanthsa S Bevinakatti, Ingleby Barwick (GB); Christian J Dederen, Meerbeek (BE); Caroline L Kelly, Northallerton (GB); Stuart Jackson, Stokesley (GB)

(73) Assignee: Croda International PLC, Goole, North Humberside (GB)

( * ) Notice: Subject to any disclaimer, the term of this patent is extended or adjusted under 35 U.S.C. 154(b) by 716 days.

(21) Appl. No.: 11/587,043

(22) PCT Filed: Apr. 12, 2005

(86) PCT No.: PCT/GB2005/001389
§ 371 (c)(1),
(2), (4) Date: Aug. 13, 2008

(87) PCT Pub. No.: WO2005/102265
PCT Pub. Date: Nov. 3, 2005

(65) Prior Publication Data
US 2009/0012185 A1 Jan. 8, 2009

(30) Foreign Application Priority Data
Apr. 23, 2004 (GB) .................................. 0409066.8

(51) Int. Cl.
*A01N 25/00* (2006.01)
*A61K 47/00* (2006.01)
*A61K 8/02* (2006.01)

(52) U.S. Cl.
USPC .......................................... 514/785; 424/401

(58) Field of Classification Search
USPC .......................................... 514/785; 424/401
See application file for complete search history.

(56) References Cited

U.S. PATENT DOCUMENTS

| 4,022,938 A | 5/1977 | Zaki et al. |
| 4,297,290 A * | 10/1981 | Stockburger .................. 549/478 |
| 6,096,325 A * | 8/2000 | Date et al. ..................... 424/401 |
| 2003/0203070 A1 | 10/2003 | Lin et al. |

FOREIGN PATENT DOCUMENTS

| DE | 2335549 A1 | 2/1975 |
| WO | WO 2004/111168 A1 | 12/2004 |

OTHER PUBLICATIONS

Satomi et al. JP 5073456. Issued Oct. 14, 1993.*
International Search Report dated Jul. 13, 2005 for PCT/GB2005/001389.
Abstract: "The use of Ariatone LC in personal care formulations" Jul. 30, 2004, Chemical Abstracts Service, Columbus, Ohio XP002334226 (STN Database Accession No. 2004:606896).
Abstract: Satokmi, Nobuyuki "Storage-stable organic peroxide emulsions as initiators for polymerization" Oct. 27, 1990, Chemical Abstracts Service, Columbus, Ohio XP00234227 (STN Database Accession No. 1990:553266).

* cited by examiner

*Primary Examiner* — Gina C Justice
*Assistant Examiner* — Genevieve S Alley
(74) *Attorney, Agent, or Firm* — Jones Day

(57) ABSTRACT

A surfactant composition contains at least one sorbitan ester and at least one sorbitol ester wherein the mean number of carbon atoms of the hydrophobe of the sorbitan ester is greater than that of the sorbitol ester. The surfactant composition is particularly suitable for use in stabilizing emulsions, especially personal care or cosmetic products.

22 Claims, No Drawings

SURFACTANT COMPOSITION

CROSS REFERENCE TO RELATED APPLICATION

This application is the National Phase application of International Application No. PCT/GB2005/001389, filed Apr. 23, 2005, which designates the United States and was published in English. This application, in its entirety, is incorporated herein by reference.

FIELD OF INVENTION

The present invention relates to a surfactant composition comprising a sorbitan-ester and a sorbitol ester, to an emulsion formed using the surfactant composition, and in particular to a personal care or cosmetic product formed from the emulsion.

BACKGROUND

Sorbitan esters have been used for many years as surface active agents, having emulsifying, dispersing, wetting and/or solubilising properties in a wide range of applications such as personal care, cleaning, general industrial, food, and many others. In particular, sorbitan esters have been used as emulsifiers in personal care applications, for example skin care, sunscreens, toiletries, decorative cosmetics, perfumes and fragrances.

Commercial production of sorbitan esters normally involves the reaction of sorbitol with fatty acids or derivatives thereof, and results in a complex mixture of products including sorbitol mono- di-, tri-, and higher esters, sorbitan mono-, di-, and higher-esters, isosorbide mono-, and di-esters, and non-esterified sorbitol, sorbitan and isosorbide. The concentrations of the aforementioned individual components can vary, but sorbitan esters are the main components. There can be significant amounts of isosorbide esters present, but sorbitol esters are normally present at very low concentrations. The number of carbon atoms present in the hydrophobe of the sorbitol/sorbitan/isosorbide esters is dependant upon the particular fatty acid(s) employed in the reaction, and the average number thereof will be substantially the same for all of the components.

Current commercially available sorbitan esters are effective emulsifiers in many applications, but there is still a requirement to improve the properties thereof, particularly in personal care applications, such as flexibility of use, improved water resistance, smooth and light skin feel, and spreading properties. Often an additional co-emulsifier is required to be used with sorbitan esters, and there would be significant advantages if a sorbitol based self-emulsifying system could be developed, i.e. without the need for a co-emulsifier, particularly one capable of forming liquid crystals in water, and especially in oil in water emulsions.

SUMMARY OF THE INVENTION

We have now surprisingly discovered a surfactant composition which overcomes or significantly reduces at least one of the aforementioned problems.

Accordingly, the present invention provides a surfactant composition comprising at least one sorbitan ester and at least one sorbitol ester wherein the mean number of carbon atoms of the hydrophobe of the sorbitan ester is greater than that of the sorbitol ester.

The invention also provides a method of forming a surfactant composition which comprises mixing together a sorbitan ester component and a sorbitol ester component wherein the mean number of carbon atoms of the hydrophobe of the sorbitan ester is greater than that of the sorbitol ester.

The invention further provides an emulsion comprising a surfactant composition capable of forming liquid crystals in water which comprises at least one sorbitan ester and at least one sorbitol ester wherein the mean number of carbon atoms of the hydrophobe of the sorbitan ester is greater than that of the sorbitol ester.

The invention further provides a personal care or cosmetic product comprising a surfactant composition comprising at least one sorbitan ester and at least one sorbitol ester wherein the mean number of carbon atoms of the hydrophobe of the sorbitan ester is greater than that of the sorbitol ester.

The invention still further provides the use of a surfactant composition comprising at least one sorbitan ester and at least one sorbitol ester wherein the mean number of carbon atoms of the hydrophobe of the sorbitan ester is greater than that of the sorbitol ester, to stabilise an emulsion.

The invention yet further provides the use of a surfactant composition comprising at least 3% by weight of at least one sorbitol ester, to form liquid crystals in the water phase of an oil in water emulsion, to stabilise the emulsion.

The sorbitan and/or sorbitol esters used in the present invention are normally made by reacting sorbitol with fatty acids or derivatives thereof, e.g. fatty acid methyl, ethyl and/or isopropyl esters, or fatty acid triglycerides. Preferred fatty acids comprise in the range from 8 to 24, more preferably 10 to 22, particularly 12 to 20, and especially 12 to 18 carbon atoms. Linear fatty acids are preferred. Suitable fatty acids include capric, lauric, myristic, palmitic, stearic, and/or behenic acid.

In a preferred embodiment greater than 80%, more preferably greater than 85%, particularly greater than 90%, and especially greater than 95% by weight of saturated fatty acids are employed. The concentration of unsaturated fatty acids used is preferably less than 20%, more preferably less than 15%, particularly less than 10%, and especially less than 5% by weight. Oleic acid is a particularly suitable unsaturated fatty acid.

The mean number of carbon atoms (on a molar basis) present in the hydrophobe (derived from the fatty acid or derivative thereof) of the sorbitan esters is suitably at least 1, preferably at least 2, more preferably in the range from 3 to 7, particularly 4 to 6, and especially 4.5 to 5 greater than the mean number of carbon atoms present in the hydrophobe of the sorbitol esters. The mean number of carbon atoms of the sorbitan ester hydrophobe is suitably in the range from 12 to 24, preferably 14 to 20, more preferably 15 to 19, particularly 16 to 18, and especially 16.5 to 17.5. The mean number of carbon atoms of the sorbitol ester hydrophobe is suitably in the range from 8 to 20, preferably 10 to 16, more preferably 11 to 14, particularly 11.5 to 13, and especially 12 to 12.5.

The ratio of sorbitan esters to sorbitol esters present in a composition according to the present invention is suitably in the range from 1 to 50:1, preferably 2 to 30:1, more preferably 4 to 20:1, particularly 7 to 13:1, and especially 9 to 11:1 by weight.

The concentration of sorbitan esters is suitably in the range from 25 to 95%, preferably 45 to 90%, more preferably 60 to 85%, particularly 65 to 80%, and especially 69 to 73% by weight of the total composition. The concentration of sorbitol esters is suitably in the range from 1 to 25%, preferably 3 to 15%, more preferably 5 to 12%, particularly 7 to 9%, and especially 7.5 to 8.5% by weight of the total composition. The concentration of isosorbide esters is suitably in the range from 3 to 35%, preferably 7 to 25%, more preferably 10 to 20%, particularly 14 to 18%, and especially 15 to 17% by weight of the total composition.

Suitable sorbitan esters include sorbitan cocoate, sorbitan caprate, sorbitan laurate, sorbitan myristate, sorbitan palmitate and/or sorbitan stearate. Preferred sorbitan esters are sorbitan palmitate and/or sorbitan stearate.

In a particularly preferred embodiment, the concentration of sorbitan palmitate and/or sorbitan stearate is at least 70%, more preferably at least 90%, particularly at least 95%, and especially at least 98% by weight of the total concentration of sorbitan esters present in the composition. When present as a mixture, the molar ratio of sorbitan palmitate to sorbitan stearate is preferably in the range from 0.3 to 4:1, more preferably 0.5 to 2:1, particularly 0.7 to 1.5:1, and especially 0.9 to 1.1:1.

A preferred minor sorbitan ester component is sorbitan laurate which is preferably present at a concentration of less than 5%, more preferably less than 3%, particularly in the range from 0.2 to 2%, and especially 0.5 to 1.5% by weight of the total concentration of sorbitan esters.

The sorbitan esters used in the present invention preferably comprise a mixture of mono-, di-, tri-, and optionally tetra-, esters. The concentration of monoesters is suitably at least 20%, preferably at least 25%, more preferably at least 30%, particularly at least 35%, and especially at least 40% by weight based upon the total concentration of sorbitan esters. The concentration of the combination of monoesters and diesters is suitably at least 50%, preferably at least 65%, more preferably at least 75%, particularly at least 80%, and especially at least 85% by weight based upon the total concentration of sorbitan esters. Correspondingly, the concentration of tri- and tetra-esters is suitably not more than 50%, preferably not more than 35%, more preferably not more than 25%, particularly not more than 20%, and especially not more than 15% by weight based upon the total concentration of sorbitan esters.

Suitable sorbitol esters include sorbitol cocoate, sorbitol caprate, sorbitol laurate, sorbitol myristate, sorbitol palmitate and/or sorbitol stearate, preferably sorbitol laurate, sorbitol palmitate and/or sorbitol stearate, and more preferably sorbitol laurate.

In a preferred embodiment, the concentration of sorbitol laurate is suitably in the range from 0.5 to 25%, preferably 2 to 15%, more preferably 4 to 10%, particularly 6 to 8%, and especially 6.5 to 7.5% by weight of the total composition. In addition, the concentration of sorbitol laurate is suitably at least 30%, preferably at least 50%, more preferably at least 70%, particularly at least 80%, and especially at least 90% by weight of the total concentration of sorbitol esters present in the composition. Further, the concentration of sorbitol laurate is preferably at least 1, more preferably at least 5, particularly at least 7, and especially at least 10 times by weight greater than any other individual sorbitol ester present in the composition. Thus, sorbitol laurate is preferably the predominant sorbitol ester present in the composition.

Preferred minor sorbitol esters are sorbitol palmitate and/or sorbitol stearate, suitably present at a combined concentration of less than 7%, preferably less than 5%, more preferably less than 3%, particularly less than 1%, and especially less than 0.5% by weight of the total composition.

The sorbitol esters used in the present invention preferably comprise a mixture of mono- and di-esters. The concentration of monoesters is suitably at least 40%, preferably at least 60%, more preferably at least 70%, particularly at least 80%, and especially at least 85% by weight based upon the total concentration of sorbitol esters. The concentration of diesters is suitably less than 60%, preferably less than 40%, more preferably less than 30%, particularly less than 20%, and especially less than 15% by weight based upon the total concentration of sorbitol esters.

The concentration of free polyol, preferably sorbitol, sorbitan and/or isosorbide, present in a composition according to the present invention is suitably in the range from 0.5 to 20%, preferably 2 to 15%, more preferably 3 to 10%, particularly 4.5 to 6%, and particularly 5 to 5.5% by weight of the total composition. Suitably greater than 20%, preferably in the range from 30 to 80%, more preferably 35 to 70%, particularly 40 to 60%, and especially 45 to 55% by weight of the free polyol is sorbitol.

The surfactant composition according to the present invention is preferably formed by mixing together (i) a composition predominantly comprising sorbitan ester (hereinafter referred to as the sorbitan ester component), and (ii) a composition predominantly comprising sorbitol ester (hereinafter referred to as the sorbitol ester component).

The sorbitan ester component suitably comprises sorbitan ester at a concentration in the range from 25 to 98%, preferably 45 to 90%, more preferably 65 to 85%, particularly 74 to 82%, and especially 76 to 80% by weight of the total composition.

Suitable sorbitan esters include sorbitan cocoate, sorbitan caprate, sorbitan laurate, sorbitan myristate, sorbitan palmitate and/or sorbitan stearate. Preferred sorbitan esters are sorbitan palmitate and/or sorbitan stearate.

The concentration of sorbitan palmitate and/or sorbitan stearate is preferably at least 75%, more preferably at least 92%, particularly at least 97%, and especially at least 99% by weight of the total concentration of sorbitan esters present in the sorbitan ester component. The preferred molar ratios, when present as a mixture, of sorbitan palmitate to sorbitan stearate in the sorbitan ester component are the same as those given above for the surfactant composition according to the present invention.

The preferred concentration ranges of sorbitan monoesters, diesters, and higher esters in the sorbitan ester component are the same as those given above for the surfactant composition according to the present invention.

The concentration of sorbitol ester in the sorbitan ester component is suitably less than 10%, preferably less than 6%, more preferably less than 3%, particularly less than 1%, and especially less than 0.5% by weight of the total composition. The sorbitol ester suitably comprises sorbitol palmitate and/or sorbitol stearate, preferably present at a molar ratio in the range from 0.3 to 4:1, more preferably 0.5 to 2:1, particularly 0.7 to 1.5:1, and especially 0.9 to 1.1:1.

The concentration of isosorbide esters in the sorbitan ester component is suitably in the range from 3 to 40%, preferably 8 to 30%, more preferably 12 to 25%, particularly 16 to 20%, and especially 17 to 19% by weight of the total composition.

The concentration of free polyol, preferably sorbitol, sorbitan and/or isosorbide, present in the sorbitan ester component is suitably in the range from 0.5 to 15%, preferably 1 to 10%, more preferably 1.5 to 6%, particularly 2 to 4%, and particularly 2.5 to 3.5% by weight. Preferably greater than 30%, more preferably in the range from 50 to 95%, particularly 60 to 85%, and especially 70 to 80% by weight of the free polyol is sorbitan.

The sorbitan ester component suitably has a HLB value in the range from 3 to 10, preferably 3.5 to 8, more preferably 4 to 6, particularly 4.4 to 5, and especially 4.6 to 4.8.

The concentration of sorbitol ester in the sorbitol ester component is suitably at least 25%, preferably in the range from 40 to 95%, more preferably 50 to 85%, particularly 60 to 80%, and especially 65 to 75% by weight of the total composition.

Suitable sorbitol esters include sorbitol cocoate, sorbitol caprate, sorbitol laurate, sorbitol myristate, sorbitol palmitate and/or sorbitol stearate, and preferably sorbitol laurate.

The concentration of sorbitol laurate is preferably at least 50%, more preferably at least 80%, particularly at least 90%, and especially at least 95% by weight of the total amount of sorbitol esters present in the sorbitol ester component.

The concentration of sorbitan ester, preferably sorbitan laurate, in the sorbitol ester component is suitably less than 30%, preferably in the range from 1 to 20%, more preferably 3 to 12%, particularly 5 to 9%, and especially 6 to 8% by weight of the total composition.

The concentration of free polyol, preferably sorbitol, sorbitan and/or isosorbide, present in the sorbitol ester component is preferably in the range from 2 to 60%, more preferably 10 to 50%, particularly 15 to 40%, and particularly 20 to 30% by weight of the total composition. Preferably greater than 50%, more preferably greater than 75%, particularly greater than 85%, and especially greater than 95% by weight of the free polyol in the sorbitol ester component is sorbitol.

The preferred concentration ranges of sorbitol monoesters and diesters in the sorbitol ester component are the same as those given above for the surfactant composition according to the present invention.

In order to form a surfactant composition according to the present invention, the sorbitan ester component is suitably mixed together with the sorbitol ester component at a weight ratio in the range from 0.5 to 100:1, preferably 3 to 50:1, more preferably 7 to 15:1, particularly 8 to 10:1, and especially 8.5 to 9.5:1.

The surfactant composition according to the present invention is capable of forming liquid crystals in water, preferably forms liquid crystals, more preferably in emulsions, and particularly in oil in water emulsions. The liquid crystals which are formed are preferably lyotropic liquid crystals (i.e. both concentration and temperature dependant), more preferably lamellar phase liquid crystals, and particularly L alpha phase (neat) liquid crystals.

The surfactant composition is suitable for use in forming emulsions (and dispersions), i.e. as the, or as part of the, emulsifier system, such as water in oil emulsions, oil in polyol (e.g. glycerol) emulsions, particularly oil in water emulsions, and especially for use in personal care or cosmetic products.

The oil phase of the emulsion according to the present invention will preferably mainly be an emollient oil of the type used in personal care or cosmetic products. The emollient can and usually will be an oily material which is liquid at ambient temperature. Alternatively it can be solid at ambient temperature, in which case in bulk it will usually be a waxy solid, provided it is liquid at an elevated temperature at which it can be included in and emulsified in the composition. The manufacture of the composition preferably uses temperatures up to 100° C., more preferably about 80° C., and therefore such solid emollients will preferably have melting temperatures of less than 100° C., and more preferably less than 70° C.

Suitable normally liquid emollient oils include non-polar oils, for example mineral or paraffin, especially isoparaffin, oils, such as that sold by Uniqema as Arlamol (trade mark) HD; or medium polarity oils, for example vegetable ester oils such as jojoba oil, vegetable glyceride oils, animal glyceride oils, such as that sold by Uniqema as Estol (trade mark) 3603 (caprylic/capric triglyceride), synthetic oils, for example synthetic ester oils, such as isopropyl palmitate and those sold by Uniqema as Estol 1512 and Arlamol DOA, ether oils, particularly of two fatty e.g. C8 to C18 alkyl residues, such as that sold by Cognis as Cetiol OE (dicaprylether), guerbet alcohols such as that sold by Cognis as Eutanol G (octyl dodecanol), or silicone oils, such as dimethicone oil such as those sold by Dow Corning as DC200, cyclomethicone oil, or silicones having polyoxyalkylene side chains to improve their hydrophilicity; or highly polar oils including alkoxylate emollients for example fatty alcohol propoxylates such as that sold by Uniqema as Arlamol E (propoxylated stearyl alcohol). Suitable emollient materials that can be solid at ambient temperature but liquid at temperatures typically used to make the compositions of this invention include jojoba wax, tallow and coconut wax/oil. When non-polar oils are used it may be desirable to use relatively high concentrations of surfactant composition according to the present invention, in order to achieve suitably satisfactory emulsification, particularly to obtain small oil droplets.

Mixtures of emollients can and often will be used, and in some cases solid emollients may dissolve wholly or partly in liquid emollients or in combination the freezing point of the mixture is suitably low. Where the emollient composition is a solid (such as fatty alcohols) at ambient temperature, the resulting dispersion may technically not be an emulsion (although in most cases the precise phase of the oily disperse phase cannot readily be determined) but such dispersions behave as if they were true emulsions and the term emulsion is used herein to include such compositions.

The concentration of the oil phase may vary widely. The amount of oil in the emulsion is suitably in the range from 1 to 90%, preferably 3 to 60%, more preferably 5 to 40%, particularly 8 to 20%, and especially 10 to 15% by weight of the total composition.

The amount of water (or polyol, e.g. glycerin) present in the emulsion is suitably greater than 5%, preferably in the range from 30 to 90%, more preferably 50 to 90%, particularly 70 to 85%, and especially 75 to 80% by weight of the total composition. The amount of surfactant composition defined herein in an emulsion or personal care or cosmetic product according to the present invention is suitably in the range from 0.1 to 10%, preferably 0.5 to 8%, more preferably 1 to 7%, particularly 1.5 to 6%, and especially 2 to 5.5%, by weight of the total composition.

The emulsions according to the present invention may also contain other additional surfactant materials which form part of the emulsifier system. Other suitable surfactants include relatively hydrophilic surfactants, e.g. having a HLB value of greater than 10, preferably greater than 12, and relatively hydrophobic surfactants e.g. having a HLB value of less than 10, preferably less than 8. Relatively hydrophilic surfactants include alkoxylate surfactants with an average in the range from about 10 to about 100 alkylene oxide, particularly ethylene oxide residues; and relatively hydrophobic surfactants include alkoxylate surfactants preferably with an average in the range from about 3 to about 10 alkylene oxide, particularly ethylene oxide residues.

Personal care or cosmetic emulsions can be divided by viscosity into milks and lotions, which preferably have a low shear viscosity (measured at shear rates of about 0.1 to 10 $s^{-1}$ as is typically used in Brookfield viscometers) of up to 10,000 mPa·s, and creams which preferably have a low shear viscosity of more than 10,000 mPa·s. Milks and lotions preferably have a low shear viscosity in the range from 100 to 10,000, more preferably 200 to 5,000, and particularly 300 to 1,000 mPa·s. The amount of surfactant composition according to the present invention present in a milk or lotion is preferably in the range from 2 to 3% by weight of the total composition.

Creams preferably have a low shear viscosity of at least 20,000, more preferably in the range from 30,000 to 80,000, and particularly 40,000 to 70,000 mPa·s, although even higher viscosities e.g. up to about $10^6$ mPa·s, may also be used. The amount of surfactant composition present in a cream is preferably in the range from 4 to 5.5% by weight of the total composition.

The emulsions of the invention may be made by generally conventional emulsification and mixing methods. For example, the surfactant composition may be added to (i) the oil phase, which is then added to the aqueous phase, or (ii) both the combined oil and water phases, or (iii) the water phase, which is then added to the oil phase. Method (iii) is preferred. In all of these methods, the resulting mixture can then be emulsified using standard techniques. It is preferred to either heat the aqueous and oil phases usually above about 60° C., e.g. to about 80 to 85° C., or to subject the aqueous phase to high intensity mixing at lower, e.g. about ambient, temperature. Vigorous mixing and the use of moderately elevated temperatures can be combined if desired. The heating and/or high intensity mixing can be carried out before, during or after addition of the oil phase but once emulsified, care should be taken not to destroy the liquid crystal system by excessive mixing or stirring.

The emulsions can also be made by inverse emulsification methods, whereby the surfactant composition is added to either the oil phase or the aqueous phase, and the aqueous phase is mixed into the oil phase to initially form a water in oil emulsion. Aqueous phase addition is continued until the system inverts to form an oil in water emulsion. Plainly a substantial amount of aqueous phase will generally be needed to effect inversion and so this method is not likely to be used for high oil phase content emulsions. Vigorous mixing and the use of moderately elevated temperatures can be combined if desired. Heating can be carried out during or after addition of the aqueous phase and before, during or after inversion. High intensity mixing can be carried out during or after addition of the aqueous phase, and before or during inversion The emulsions may for example be microemulsions or nanoemulsions, having a mean droplet size over a wide range, preferably in the range from 10 to 10,000 nm. In one embodiment, the emulsion droplet size may be reduced, for example by high pressure homogenisation, preferably to a value in the range from 100 to 1,000 nm, more preferably 300 to 600 nm.

The emulsions according to the present invention are stable, measured as described herein, preferably for greater than one month, more preferably greater than two months, particularly greater than three months, and especially greater than four months at ambient temperature (23° C.), and also preferably at 40° C. The stability at even higher temperatures can be particularly important, and therefore the emulsion is stable, measured as described herein, suitably for greater than one week, preferably greater than two weeks, more preferably greater than 3 weeks, particularly greater than one month, and especially greater than two months at 50° C. In a particularly preferred embodiment, the liquid crystals created during emulsion formation are substantially maintained during the aforementioned time and temperature testing regimes.

Many other components may be included in the emulsions to make personal care or cosmetic compositions or products. These components can be oil soluble, water soluble or non-soluble. Examples of such materials include:

(i) preservatives such as those based on parabens (alkyl esters of 4-hydroxybenzoic acid), phenoxyethanol, substituted ureas and hydantoin derivatives e.g. those sold commercially under the trade names Germaben II Nipaguard BPX and Nipaguard DMDMH, when used preferably at a concentration in the range from 0.5 to 2% by weight of the total composition;

(ii) perfumes, when used preferably at a concentration in the range from 0.1 to 10% more preferably up to about 5%, and particularly up to about 2% by weight of the total composition;

(iii) humectants or solvents such as alcohols, polyols such as glycerol and polyethylene glycols, when used preferably at a concentration in the range from 1 to 10% by weight of the total composition;

(iv) sunfilter or sunscreen materials including organic sunscreens and/or inorganic sunscreens including those based on titanium dioxide or zinc oxide; when used preferably at a concentration in the range from 0.1% to 20%, more preferably 1 to 15%, and particularly 2 to 10% by weight of the total composition;

(v) alpha hydroxy acids such as glycolic, citric, lactic, malic, tartaric acids and their esters; self-tanning agents such as dihydroxyacetone;

(vi) antimicrobial, particularly anti-acne components such as salicylic acid;

(vii) vitamins and their precursors including: (a) Vitamin A, e.g. as retinyl palmitate and other tretinoin precursor molecules, (b) Vitamin B, e.g. as panthenol and its derivatives, (c) Vitamin C, e.g. as ascorbic acid and its derivatives, (d) Vitamin E, e.g. as tocopheryl acetate, (e) Vitamin F, e.g. as polyunsaturated fatty acid esters such as gamma-linolenic acid esters;

(viii) skin care agents such as ceramides either as natural materials or functional mimics of natural ceramides;

(ix) phospholipids, such as synthetic phospholipids or natural phospholipids, eg lecithin;

(x) vesicle-containing formulations;

(xi) germanium-containing compounds for example that sold by Uniqema as Arlamol GEO;

(xii) botanical extracts with beneficial skin care properties;

(xiii) skin whiteners such as Arlatone Dioic DCA (trade mark) sold by Uniqema, kojic acid, arbutin and similar materials;

(xiv) skin repair compounds actives such as Allantoin and similar series;

(xv) caffeine and similar compounds;

(xvi) cooling additives such as menthol or camphor;

(xvii) insect repellents such as N,N-diethyl-3-methylbenzamide (DEET) and citrus or eucalyptus oils;

(xviii) essential oils;

(xix) ethanol; and (xx) pigments, including microfine pigments, particularly oxides and silicates, e.g. iron oxide, particularly coated iron oxides, and/or titanium dioxide, and ceramic materials such as boron nitride, or other solid components, such as are used in make up and cosmetics, to give suspoemulsions, preferably used in an amount in the range from 1 to 15%, more preferably at least 5% and particularly approximately 10%.

The surfactant composition and emulsions according to the present invention are suitable for use in a wide range of compositions and end-use applications, such as moisturizers, sunscreens, after sun products, body butters, gel creams, high perfume containing products, perfume creams, baby care products, hair conditioners, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes.

Formulations containing a surfactant composition or emulsion according to the present invention may have a pH value over a wide range, preferably in the range from 3 to 13, more preferably 5 to 10, and especially 6 to 8.

One preferred embodiment is as a sunscreen which contains one or more organic sunscreens and/or inorganic sunscreens such as metal oxides, but preferably comprises at least one particulate titanium dioxide and/or zinc oxide, particularly included in the composition in the form of an aqueous and/or organic, preferably aqueous, dispersion available commercially from Uniqema under the trade marks Tioveil and Solaveil Clarus (both titanium dioxide) and Spectraveil (zinc oxide). In addition, organic sunscreens may be used together with the preferred metal oxide sunscreens, and include p-methoxy cinnamic acid esters, salicylic acid esters, p-amino benzoic acid esters, non-sulphonated benzophenone derivatives, derivatives of dibenzoyl methane and esters of 2-cyanoacrylic acid. Specific examples of useful organic sunscreens include benzophenone-1, benzophenone-2, benzophenone-3, benzophenone-6, benzophenone-8, benzophenone-12, isopropyl dibenzoyl methane, butyl methoxy dibenzoyl methane, ethyl dihydroxypropyl PABA, glyceryl PABA, octyl dimethyl PABA, octyl methoxycinnamate, homosalate, octyl salicylate, octyl triazone, octocrylene, etocrylene, menthyl anthranilate, 4-methylbenzylidene camphor, benzophenone 4, and phenyl benzimidazole sulphonic acid.

End use sunscreen formulations containing the surfactant composition according to the present invention can exhibit surprisingly improved water resistance and/or sun protection (SPF values).

In this specification the following test methods have been used.

(1) Analysis of C12 Sorbitol Esters by Reverse Phase HPLC

The test sample was dissolved in isopropyl alcohol/water and injected on a HPLC system using a Reversed Phase C8 column and an evaporative light scattering detector. The different sorbitol esters and unreacted polyol were eluted using a gradient of water and acetonitrile and indentified by their retention times. Quantification was based on peak area percent.

(a) Reagents

All reagents were of recognised analytical quality, namely isopropyl alcohol, acetonitrile, and water (all 'HiPerSolve', ex BDH).

(b) Equipment

HPLC system employed was Agilent 1100 series comprising G1379A de-gasser, G1311A quaternary pump, G1313A autosampler and G1316A column oven with a Polymer Labs PL ELS-1000 evaporative light scattering detector and Chemstation LC software. Other materials used were 28.25 ml glass vial (ex VWR 215007823), 2 ml autosampler vial (ex VWR 372111102), 11 mm autosampler vial crimp cap (ex VWR 372211134), 11 mm vial crimping tool (VWR 372340544), disposable pasteur pipettes (ex VWR 241259352), Zorbax Eclipse XDB-C8 HPLC column, 5 μm, 150 mm length×4.6 mm internal diameter (Part No 993967-906).

(c) Procedure (i) Power to Agilent 1100 series HPLC system turned on.
(ii) Solvent reservoirs topped up, as required.
(iii) Power and nitrogen supply to the Polymer labs PL ELS-1000 evaporative light scattering detector turned on.
(iv) Power to HPLC computer turned on.
(v) Software for PL ELS-1000 detector started.
(vi) The method employed had the following settings; evaporator temperature=85° C., nebuliser temperature=60° C., gas flow rate=1.0 liters/min, autozero offset=0, and time constant=0. The detector was allowed to stabilize for 20 minutes prior to use.
(vii) Software for HPLC started up.
(viii) Method was set up according to the following parameters; eluent A was water, eluent B was acetonitrile, gradient was as Table 1 below, flow=1.0 ml/min, injection volume=20 μl, column temperature=40° C., and run time=40 minutes.

TABLE 1

| | Gradient | |
|---|---|---|
| Time (min) | Water | Acetonitrile |
| 0 | 75% | 25% |
| 5 | 5% | 90% |
| 35 | 5% | 90% |
| 35.1 | 75% | 25% |
| 40 | 75% | 25% |

(ix) Approximately 50±5 mg of sample was dissolved in 10 ml of isopropyl alcohol. Gentle heating was used to speed up the dissolution process, if required. If the sample was still not in solution, a few drops of water were added until the solution was clear.
(x) Using a clean pasteur pipette, a 2 ml autosampler vial was filled with the solution and the vial closed using a crimp cap and crimping tool.
(xi) Sample vial was placed in autosampler tray.
(xii) Sample details were entered.
(xiii) Sample was run.
(d) Results All peaks in the resultant chromatogram were integrated and summed. Peak areas for polyol, and the various ester peaks were then calculated and expressed as a percentage of the total peak areas (polyol and ester component peaks were identified by LC-MS or by LC retention times of standards).

(2) Analysis of C16/C18 Sorbitan Esters by Reverse Phase HPLC

The procedure described in (1) above for sorbitol esters was employed except that (i) an Inertsil ODS-2 HPLC Column, 5 μm, 250 mm length×4.6 mm internal diameter (Chrompack Cat. No. 28408) was used, (ii) acetone was used instead of water, and (iii) the gradient was as in Table 2 below.

TABLE 2

| | Gradient | |
|---|---|---|
| Time (min) | Acetonitrile | Acetone |
| 0 | 90% | 10% |
| 25 | 10% | 90% |
| 35 | 10% | 90% |
| 36 | 90% | 10% |
| 40 | 90% | 10% |

(3) Emulsion Stability

Stability was assessed by observing the emulsions after storage at ambient temperature (23° C.), cold at 5° C. or under elevated temperature storage at 40° C. and 50° C. Measuring storage stability at 50° C. is a very severe test. The composition was stable if no visible separation of the emulsion occurred. The stability of the liquid crystals in the emulsion was also assessed by observing under a microscope using polarized light.

(4) Emulsion Viscosity

Viscosity was measured at 23° C. with a Brookfield LVT viscometer using an appropriate spindle (LV1, LV2, LV3, or LV4—depending on the viscosity of the emulsion being tested) at 6 rpm (0.1 Hz), 1 day after making the emulsions and results are quoted in mPa·s.

The invention is illustrated by the following non-limiting examples.

EXAMPLES

Example 1

(i) Preparation of Sorbitan Ester Component 400 g of a 1:1 molar mixture of palmitic and stearic acids, 290 g 70% aqueous sorbitol, 5 g 50% aqueous NaOH and 3 g 50% aqueous phosphorous acid were charged to a 1 liter flask, fitted with a stirrer, side-arm distillation, thermocouple, nitrogen sparge and a thermostatted electric mantle. The reaction mixture was heated with stirring to about 245° C. and water distilled off until the acid value was less than 10 mg KOH·g$^{-1}$ and the OH value was less than 260 mg KOH·g$^{-1}$. The product was then cooled and discharged.

The product was analysed as described herein and comprised 78% by weight of C16/C18 sorbitan esters, 18% by weight of C16/C18 isosorbide esters, <1% by weight of C16/C18 sorbitol esters, and 3% by weight of polyol.

(ii) Preparation of Sorbitol Ester Component (a) 330 g lauric acid, 390 g 70% aqueous sorbitol and 16 g of potassium carbonate were charged to a 1 liter flask, fitted with a stirrer, side-arm distillation, vacuum supply, thermocouple, nitrogen sparge and a thermostatted electric mantle. The reaction mixture was heated with stirring under vacuum to about 180° C. and water was distilled off. The reaction was continued until the acid value was less than 5 mg KOH·g$^{-1}$. The product was then cooled and discharged.

The product was analysed as described herein and comprised 7% by weight of C12 sorbitan esters, 68% by weight of C12 sorbitol esters, and 25% by weight of polyol.

(b) 140 g methyl laurate, 99 g anhydrous sorbitol and 6 g of potassium carbonate were charged to a 500 ml flask, fitted with a stirrer, side-arm distillation, vacuum supply, thermocouple and nitrogen sparge in an oil bath. The reaction mixture was heated with stirring under vacuum to about 160° C. and methanol was distilled off. The reaction was maintained at 160° C. under vacuum for about 3-4 hrs until a clear, single phase product was formed. Following a further 1 hour, the vacuum was released, the oil bath switched off and the product discharged.

The product was analysed as described herein and comprised 2% by weight of C12 sorbitan esters, 73% by weight of C12 sorbitol esters, and 25% by weight of polyol.

(c) The procedure of (ii)(b) above was repeated except that a nitrogen sparge without vacuum was employed. The product was analysed as described herein and comprised 3% by weight of C12 sorbitan esters, 69% by weight of C12 sorbitol esters, and 28% by weight of polyol.

(d) The procedure of (ii)(b) above was repeated except that 156 g methyl cocoate, 100 g anhydrous sorbitol and 5.7 g potassium carbonate were used. The product was analysed as described herein and comprised 1% by weight of C12 sorbitan esters, 50% by weight of C12 sorbitol esters, and 35% by weight of polyol.

(iii) Preparation of Sorbitan Ester and Sorbitol Ester Mixture 9 parts by weight of the sorbitan ester component produced above was heated to 80° C., and 1 part by weight of one of the sorbitol ester components produced above was added with stirring whilst maintaining the temperature at 80° C. The blended mixture was dropped onto a cool surface and removed as flake.

Example 2

Oil in Water Cooling Milk (Preservative Free)

| | % w/w |
|---|---|
| A. | |
| ARLAMOL HD (trade mark, ex Uniqema) | 3 |
| ARLAMOL E (trade mark, ex Uniqema) | 3 |
| Avocado oil | 5 |
| Wheatgerm Oil | 2 |
| Florasun 90 | 5 |
| Oxynex LM | 0.05 |
| B. | |
| Surfactant Composition (produced in Example 1(iii)) | 3.5 |
| Propylene Glycol | 2 |
| PRICERINE 9091 (trade mark, ex Uniqema) | 3 |
| Water | 53.3 |
| Keltrol F | 0.15 |
| C. | |
| Carbopol ETD 2050 (3% w/w solution) | 5 |
| D. | |
| Ethanol | 15 |

Procedure
1. Disperse the Keltrol in the water of phase B at room temperature.
2. Add other ingredients of B when a homogenous gel has been obtained.
3. Heat phase B to 80° C.
4. Homogenize B with Ultra Turrax homogeniser for 30 seconds at 6,000 rpm.
5. Return to water bath for 30 minutes at 80° C.
6. Heat phase A to 80° C.
7. Add phase C to B while stirring at 800 rpm.
8. Slowly add A to BC mixture while stirring at 800 rpm.
9. Homogenize for 1 minute with Ultra Turrax at 10,000 rpm.
10. Allow to cool to room temperature while stirring gently.
11. Add phase D when the temperature is below 40° C.
12. Neutralise with NaOH solution.

Example 3

Oil in Water Aqua Gel Cream

| | % w/w |
|---|---|
| A. | |
| ESTOL 3603 (trade mark, ex Uniqema) | 1.75 |
| ESTOL 3609 (trade mark, ex Uniqema) | 1.75 |
| ESTOL 1543 (trade mark, ex Uniqema) | 1.75 |
| ARLAMOL E (trade mark, ex Uniqema) | 1.75 |
| B. | |
| Surfactant Composition (produced in Example 1(iii)) | 2 |
| ATLAS G-2330 | 3 |
| PRICERINE 9091 (trade mark, ex Uniqema) | 2.1 |

-continued

|  | % w/w |
| --- | --- |
| Water | 81.5 |
| Carbopol ETD 2050 | 0.2 |
| C. | |
| Ethanol | 3.5 |
| Nipaguard BPX | 0.7 |

Procedure
1. Disperse Carbopol in cold water of phase B while stirring moderately.
2. Add other ingredients of B.
3. Heat phase A to 80° C.
4. Heat B to 80° C.
5. Homogenize B with Ultra Turrax homogeniser when at 80° C., for 30 seconds at 6,000 rpm.
6. Return to warm water bath for 30 minutes at 80° C.
7. Slowly add A to B while stirring at 800 rpm.
8. Homogenize for 1 minute with Ultra Turrax at 10,000 rpm.
9. Allow to cool to room temperature with gentle stirring.
10. Add phase C when temperature is below 40° C.
11. Neutralise with NaOH solution.

Example 4

Water in Oil in Water Sun Care Cream

|  | % w/w |
| --- | --- |
| A. | |
| ARLACEL 1690 (trade mark, ex Uniqema) | 2.5 |
| ARLAMOL HD (trade mark, ex Uniqema) | 2.5 |
| ESTOL 3603 (trade mark, ex Uniqema) | 7 |
| TIOVEIL 50 FCM (trade mark, ex Uniqema) | 5 |
| B. | |
| TIOVEIL AQ-G (trade mark, ex Uniqema) | 1.25 |
| Germaben II | 0.5 |
| Water | 31.25 |
| C. | |
| Surfactant Composition (produced in Example 1(iii)) | 5 |
| Water | 39.1 |
| Keltrol F | 0.4 |
| TIOVEIL AQ-G (trade mark, ex Uniqema) | 5 |
| D. | |
| Germaben II | 0.5 |

Procedure
1. Combine ingredients of phase A and heat to 80° C.
2. Combine ingredients of phase B and heat to 80° C.
3. Add B to A under Ultra Turrax homogeniser at 14,000 rpm and homogenize for 5 minutes.
4. Return the blend to 80° C.
5. Disperse the Keltrol in the water of phase C at room temperature.
6. Add Surfactant Composition when a homogenous gel is obtained.
7. Heat the blend to 80° C.
8. Homogenize with Ultra Turrax at 6000 rpm for 30 seconds.
9. Return C to 80° C. for 30 minutes.
10. Add the Tioveil to the heated C while stirring at 800 rpm.
11. Add AB to C while stirring at 800 rpm.
12. Homogenize with Ultra Turrax at 10000 rpm for 1 minute.
13. Allow to cool to room temperature while stirring at 50 rpm.
14. Add the Germaben when the temperature is below 40° C.
15. Neutralise to pH 7 (approx) with citric acid solution.

Example 5

Oil in Water Moisturizing Cream

|  | % w/w |
| --- | --- |
| A. | |
| PRIPURE 3759 (trade mark, ex Uniqema) | 5 |
| ESTOL 3609 (trade mark, ex Uniqema) | 5 |
| ESTOL 3603 (trade mark, ex Uniqema) | 5 |
| MONASIL PCA (trade mark, ex Uniqema) | 2 |
| Sweet Almond Oil | 2 |
| Lanette 22 | 2 |
| Oxynex LM | 0.05 |
| B. | |
| Surfactant Composition (produced in Example 1(iii)) | 5.5 |
| Keltrol F | 0.1 |
| PRICERINE 9091 (trade mark, ex Uniqema) | 4 |
| Water | 68.65 |
| C. | |
| Nipaguard BPX | 0.7 |

Procedure
1. Disperse the Keltrol in the water of phase B at room temperature.
2. Add other ingredients of B when a homogenous gel has been obtained.
3. Heat B to 80° C.
4. Homogenise B with Ultra Turrax homogeniser when at 80° C., for 30 seconds at 6,000 rpm.
5. Return to warm water bath for 30 minutes at 80° C.
6. Heat phase A to 80° C.
7. Slowly add A to B while stirring at 800 rpm.
8. Homogenize for 1 minute with an Ultra Turrax at 10,000 rpm.
9. Allow to cool to room temperature while stirring gently.
10. Add the Nipaguard when the temperature is below 40° C.

Example 6

Water Free Emulsion

|  | % w/w |
| --- | --- |
| A. | |
| ARLAMOL HD (trade mark, ex Uniqema) | 5 |
| ARLAMOL E (trade mark, ex Uniqema) | 1.2 |
| Dow Corning 245 Fluid | 2.8 |
| Paraffin Light Oil | 10 |
| B. | |
| Surfactant Composition (produced in Example 1(iii)) | 5.5 |
| PRICERINE 9091 (trade mark, ex Uniqema) | 74.5 |
| C. | |
| Germaben II | 1 |

Procedure
1. Heat phase B to 80° C.
2. Homogenise B at 6,000 rpm for 30 seconds.
3. Return B to 80° C. for 30 minutes.

4. Heat phase A to 80° C.
5. Add A to B under stirring at 800 rpm.
6. Homogenise with an Ultra Turrax homogeniser for 1 minute at 10,000 rpm.
7. Allow to cool to room temperature while stirring at 120 rpm.
8. Add Germaben when the temperature is below 40° C.

Example 7

Silicone in Water Emulsion

|  | % w/w |
|---|---|
| A. | |
| Dow Corning 345 Fluid | 40 |
| B. | |
| Surfactant Composition (produced in Example 1(iii)) | 5.5 |
| PRICERINE 9091 (trade mark, ex Uniqema) | 4 |
| Water | 49.7 |
| C. | |
| Keltrol F | 0.1 |
| D. | |
| Nipaguard BPX | 0.7 |

Procedure
1. Disperse the Keltrol in the water at room temperature.
2. Add the remaining ingredients of phase B when a homogeneous gel is obtained.
3. Heat the blend B to 80° C.
4. Homogenise B at 6,000 rpm for 30 seconds.
5. Return B to a warm water bath at 80° C. for 30 minutes.
6. Heat phase A to 80° C.
7. Add A to B under stirring at 800 rpm.
8. Homogenise with an Ultra Turrax homogeniser for 1 minute at 10,000 rpm.
9. Allow to cool to room temperature while stirring at 120 rpm.
10. Add the Nipaguard when the temperature is below 40° C.

Example 8

Oil in Water Aqua Gel Sunscreen Cream

|  | % w/w |
|---|---|
| A. | |
| Dow Corning 245 Fluid | 4 |
| ESTOL 1543 (trade mark, ex Uniqema) | 4 |
| Dow Corning 200-100 c.St | 2 |
| PRISORINE 2021 (trade mark, ex Uniqema) | 5 |
| MONASIL PCA (trade mark, ex Uniqema) | 1.5 |
| B. | |
| SOLAVEIL CT-200 (trade mark, ex Uniqema) | 15 |
| C. | |
| Surfactant Composition (produced in Example 1(iii)) | 5 |
| Carbopol Ultrez 10 | 0.2 |
| Veegum Ultra | 0.8 |
| MONAMATE RMEA 40 (trade mark, ex Uniqema) | 0.2 |
| Propylene glycol | 4 |
| Water | 57.7 |

-continued

|  | % w/w |
|---|---|
| D. | |
| Sodium Hydroxide (30% w/w solution) | q.s. |
| E. | |
| Fragrance | 0.3 |
| Liquid Germall Plus | 0.3 |

Procedure
1. Disperse Carbopol in water. When fully dispersed add in Veegum Ultra and disperse again.
2. Add the rest of ingredients of phase C and heat to 80° C.
3. When C has reached 80° C., homogenise for 30 seconds and continue to heat at 80° C. for another 20 minutes.
4. Combine all ingredients of phase A and heat to 75-80° C.
5. Add phase B into A with high sheer mixing while maintaining the temperature at 75-80° C.
6. Add A/B mixture into C with high sheer mixing and homogenise at 10,000 rpm for 1 minute.
7. Adjust pH to 6.5-7.0 with sodium hydroxide.
8. Continue to cool down to room temperature with stirring.

The resultant opaque cream showed no visible separation after 3 months storage at 5° C., ambient temperature (23° C.), and at 40° C. The cream showed no visible separation after 1 month at 50° C.

The invention claimed is:
1. A liquid-crystal forming surfactant composition comprising:
   a) a sorbitan ester component comprising at least one sorbitan fatty acid ester; and
   b) a sorbitol ester component comprising at least one sorbitol fatty acid ester; wherein:
      i) the fatty acid residue of the at least one sorbitan fatty acid ester has a greater mean number of carbon atoms than that of the fatty acid residue of the at least one sorbitol fatty acid ester;
      ii) the fatty acid residue of the at least one sorbitan fatty acid ester and the fatty acid residue of the at least one sorbitol fatty acid ester have a saturated fatty acid content of greater than 80% by weight; and
      iii) the surfactant composition forms liquid crystals in water.
2. The composition of claim 1, wherein the mean number of carbon atoms of the fatty acid residue of the at least one sorbitan fatty acid ester is at least 2 carbon atoms greater than that of the fatty acid residue of the at least one sorbitol fatty acid ester.
3. The composition of claim 1, wherein the mean number of carbon atoms of the fatty acid residue of the at least one sorbitan fatty acid ester is 3 to 7 carbon atoms greater than that of the fatty acid residue of the at least one sorbitol fatty acid ester.
4. The composition of claim 1, wherein the mean number of carbon atoms of the fatty acid residue of the at least one sorbitan fatty acid ester is 15 to 19 and/or the mean number of carbon atoms of the fatty acid residue of the at least one sorbitol fatty acid ester is 11 to 14.
5. The composition of claim 1, wherein the ratio of sorbitan fatty acid esters to sorbitol fatty acid esters is 4 to 20:1 by weight.
6. The composition of claim 1, wherein the composition comprises:
   a) 45 to 90% by weight of the at least one sorbitan fatty acid ester;

b) 3 to 15% by weight of the at least one sorbitol fatty acid ester; and/or c) 7 to 25% by weight of isosorbide fatty acid esters.

7. The composition of claim 1, wherein the sorbitan ester component comprises sorbitan palmitate and/or sorbitan stearate and the sorbitol ester component comprises sorbitol laurate.

8. The composition of claim 7, wherein the composition comprises 2 to 15% by weight of the sorbitol laurate.

9. The composition of claim 7, wherein the sorbitol laurate comprises at least 70% by weight of the sorbitol ester component.

10. The composition of claim 1, wherein the sorbitol ester component comprises:

a) at least 60% of sorbitol fatty acid monoesters; and b) less than 40% by weight of sorbitol fatty acid diesters.

11. The composition of claim 1, wherein the composition comprises 2 to 15% by weight of polyol.

12. The composition of claim 11, wherein 30 to 80% by weight of the polyol is sorbitol.

13. A method of forming the liquid-crystal forming surfactant composition of claim 1, comprising mixing together the sorbitan ester component and the sorbitol ester component.

14. The method of claim 13, wherein the sorbitan ester component comprises 65 to 85% by weight of the at least one sorbitan fatty acid ester.

15. The method of claim 13, wherein the sorbitol ester component comprises 50 to 85% by weight of the at least one sorbitol fatty acid ester.

16. An emulsion comprising the liquid-crystal forming surfactant composition of claim 1.

17. The emulsion of claim 16, wherein the emulsion comprises 1 to 7% by weight of the liquid-crystal forming surfactant composition.

18. The emulsion of claim 16, comprising liquid crystals which are stable for greater than 3 months at ambient temperature, and/or greater than 2 months at 40° C., and/or greater than 1 month at 50° C.

19. The emulsion of claim 16, wherein the emulsion is stable for greater than 4 months at ambient temperature, and/or greater than 3 months at 40° C., and/or greater than 2 months at 50° C.

20. A personal care or cosmetic product comprising the liquid-crystal forming surfactant composition of claim 1.

21. A method of using the liquid-crystal forming surfactant composition of claim 1 to stabilize an emulsion, comprising mixing said liquid-crystal forming surfactant composition with the emulsion.

22. The method of claim 21, wherein the liquid-crystal forming surfactant composition:

a) comprises at least 3% by weight of the at least one sorbitol fatty acid ester;

b) stabilizes an oil in water emulsion; and c) forms liquid crystals in the water phase of the oil in water emulsion.

* * * * *